US012733859B2

(12) United States Patent
Teplitzky

(10) Patent No.: US 12,733,859 B2
(45) Date of Patent: Sep. 15, 2026

(54) SYNTHETIC DATA AUGMENTATION FOR ECG USING DEEP LEARNING

(71) Applicant: Preventice Solutions, Inc., Rochester, MN (US)

(72) Inventor: Benjamin A. Teplitzky, Minneapolis, MN (US)

(73) Assignee: BOSTON SCIENTIFIC CARDIAC DIAGNOSTICS, INC., Rochester, MN (US)

( * ) Notice: Subject to any disclaimer, the term of this patent is extended or adjusted under 35 U.S.C. 154(b) by 621 days.

(21) Appl. No.: 18/099,484

(22) Filed: Jan. 20, 2023

(65) Prior Publication Data

US 2023/0225660 A1 Jul. 20, 2023

Related U.S. Application Data

(60) Provisional application No. 63/301,238, filed on Jan. 20, 2022.

(51) Int. Cl.
*A61B 5/00* (2006.01)
*A61B 5/318* (2021.01)

(52) U.S. Cl.
CPC ............ *A61B 5/318* (2021.01); *A61B 5/7267* (2013.01); *A61B 5/7278* (2013.01); *A61B 5/7282* (2013.01)

(58) Field of Classification Search
CPC ..... A61B 5/318; A61B 5/7267; A61B 5/7278; A61B 5/7282
See application file for complete search history.

(56) References Cited

U.S. PATENT DOCUMENTS

2021/0174961 A1* 6/2021 Dutt ....................... G16H 50/20

FOREIGN PATENT DOCUMENTS

WO WO-2020006939 A1 * 1/2020 ........... G06K 9/6256

OTHER PUBLICATIONS

Delaney Et al., “Synthesis of Realistic ECG Using Generative Adversarial Networks”, arXiv:1909.09150v1 [eess.SP] Sep. 19, 2019, Sep. 23, 2019, pp. 1-16.

International Search Report and Written Opinion received for PCT Patent Application No. PCT/US23/11231, mailed on May 11, 2023, 11 pages.

* cited by examiner

*Primary Examiner* — Sana Sahand

(74) *Attorney, Agent, or Firm* — Faegre Drinker Biddle & Reath LLP

(57) ABSTRACT

A method includes generating first electrocardiogram (ECG) data by adding synthetic noise to naturally occurring ECG data using a first deep neural network (DNN). The method further includes providing one of: (i) the first ECG data, or (ii) second ECG data including naturally occurring noise, to a second DNN. An output is generated by the second DNN indicating whether the second DNN received the first ECG data or the second ECG data.

19 Claims, 7 Drawing Sheets

SYNTHETIC DATA AUGMENTATION FOR ECG USING DEEP LEARNING

CROSS REFERENCE TO RELATED APPLICATION

This application claims priority to Provisional Application No. 63/301,238, filed Jan. 20, 2022, which is herein incorporated by reference in its entirety.

BACKGROUND

Portable monitoring devices for collecting biometric data are becoming increasingly common in diagnosing and treating medical conditions in patients. Mobile cardiac telemetry (MCT) is one example of this. MCT empowers physicians with valuable information regarding the occurrence and regularity of a variety of heart conditions and irregularities. ECG data collected using MCT can be analyzed to detect a variety of cardiac conditions, including various irregular heartbeats and heart rhythms.

Machine learning (ML) models can be used to analyze ECG data collected using MCT and detect cardiac conditions. For example, a variety of supervised deep learning ML models can be used. But supervised ML models rely on appropriate training data to train the model and allow for accurate inference. Identifying a sufficiently large set of naturally occurring ECG training data can be difficult, time consuming, and expensive. Artificial ECG training data can, by contrast, be generated relatively inexpensively, but is challenging because ECG data includes non-stationary and complex noise. Leaving out this naturally occurring noise from artificially created ECG training data results in significant inaccuracy in a trained ML model, and accurately replicating the noise is very difficult.

BRIEF DESCRIPTION OF THE DRAWINGS

So that the manner in which the features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DESCRIPTION OF EXAMPLE EMBODIMENTS

Figure 1:
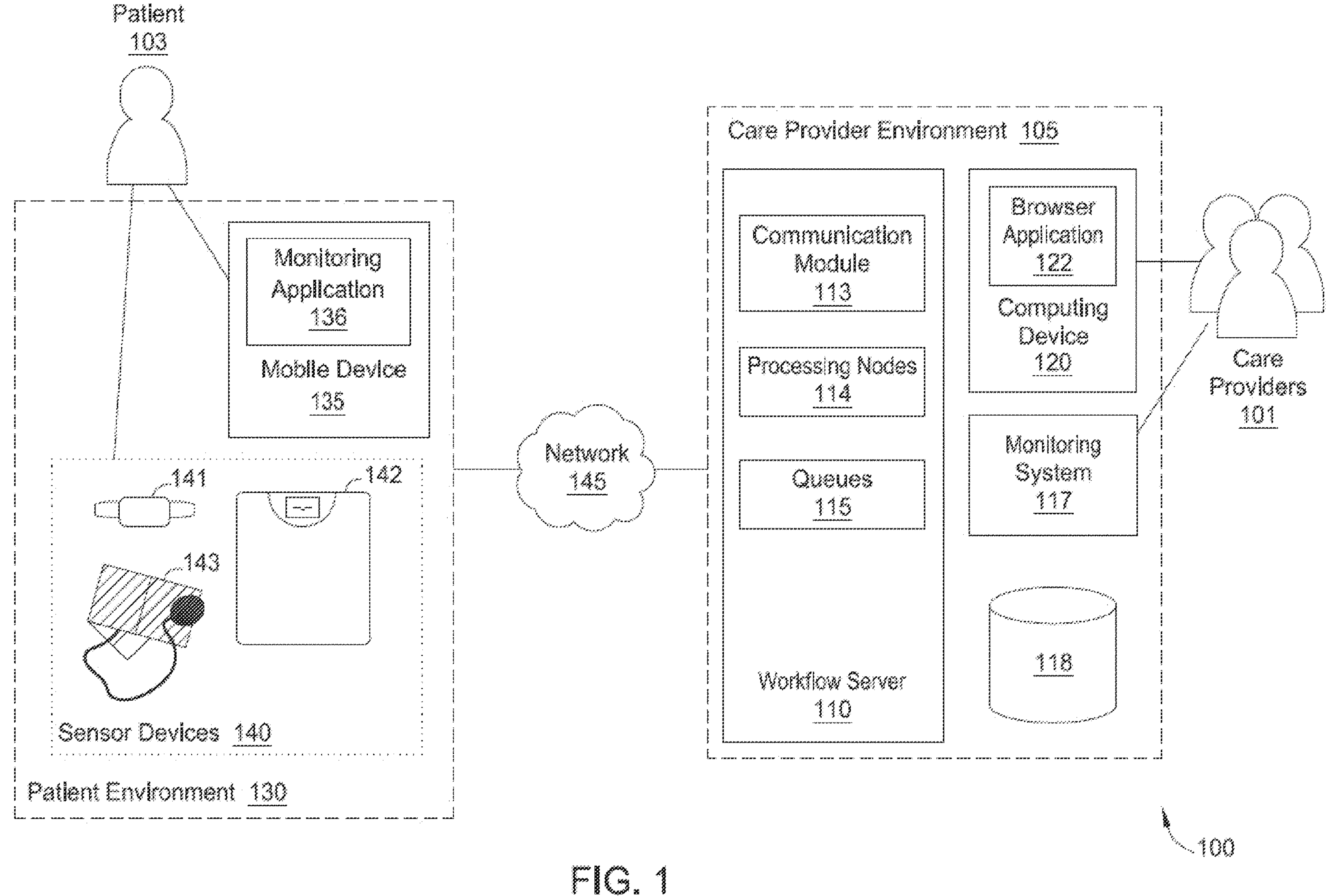
FIG. 1 illustrates an example computing environment, according to certain embodiments of the present disclosure.

Interpreting patient ECG data can be difficult and time consuming. Deep learning techniques can allow for accurate and speedy identification of cardiac events (e.g., abnormal heart beats and heart rhythms) in ECG data. But identifying a large body of naturally occurring ECG training data is often extremely difficult, or impossible. And generating artificial ECG training data is also extremely difficult, because naturally occurring ECG data typically includes non-stationary and complex noise.

In an embodiment, deep learning ML models can, themselves, be used to generate artificial ECG training data with realistic noise. For example, generative adversarial networks (GANs) can generate realistic synthetic data for some applications. Realistic synthetic data can then be used to improve performance of deep learning algorithms by synthetically increasing the volume of training data. While there exist a number of more common and less sophisticated techniques for synthetically increasing training data volume (e.g. data augmentation or synthetic minority oversampling technique (SMOTE)) these techniques require the data to be manually augmented (for example, data augmentation by adding synthetic and often unrealistic noise), or modified using artificial creation of features (SMOTE), which is not helpful for training important upper layers of the network, where feature extraction occurs.

This is particularly true for ECG data, because noisy ECG data can be especially important for training an ML model to identify and classify cardiac irregularities. Many ML models have great difficulty analyzing noisy ECG data, and so they must be trained with a large quantity of realistically noisy ECG data. Thus, providing realistic synthetic noise for training data significantly improves accuracy and performance. And, by contrast, providing unrealistic synthetic noise during training can significantly damage accuracy and performance.

In an embodiment, GANs can be used train a network to ingest raw ECG, which has already been annotated, and output an augmented version of the same ECG where the labels remain true but realistic noise has been added by the network. This allows for rapid creation of large datasets for training, from a small dataset. Further, in an embodiment, the network can be seeded with a random number vector, causing the added noise to vary. This means that many augmented examples can be created from a single natural ECG record.

Additionally, because the techniques begin with a natural ECG recording, in embodiments the input ECG can be used together with the output ECG to evaluate the performance of filtering pipelines (e.g., filtering pipelines to remove naturally occurring noise from ECG). A filtering pipeline, applied to the augmented ECG, can end up looking similar to the input ECG. This can be quantified by using a variety of techniques, for example measuring correlation between the natural ECG and the filtered noisy ECG.

In an embodiment, a GAN architecture can be used to build a deep learning network that ingests raw ECG and produces a realistically noisy version of the same ECG. In biological signals like ECG, noise is generally non-stationary and complex. In ECG, noise originates from several sources including power line interference, muscle activity, varying integrity of the tissue-electrode interface, movement, analog to digital conversion, signal hardware filtering, and data transmission. Current approaches to introducing synthetic noise to ECG typically rely on random addition in the frequency domain using white or pink noise or using isolated noise from real ECG recordings. The result of these methods generally looks very unrealistic. Using the GAN architecture, we connect two deep neural networks (DNNs), one that ingests clean ECG and is meant to learn how to create noisy ECG, and another whose purpose is to determine whether it is passed a real example of noisy ECG or a synthetically noisy ECG. The two networks are co-trained and improve each other as training continues.

FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a dedicated computing system or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicating an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if they have any symptoms or instructing the patient 103 to reattach a disconnected electrode of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
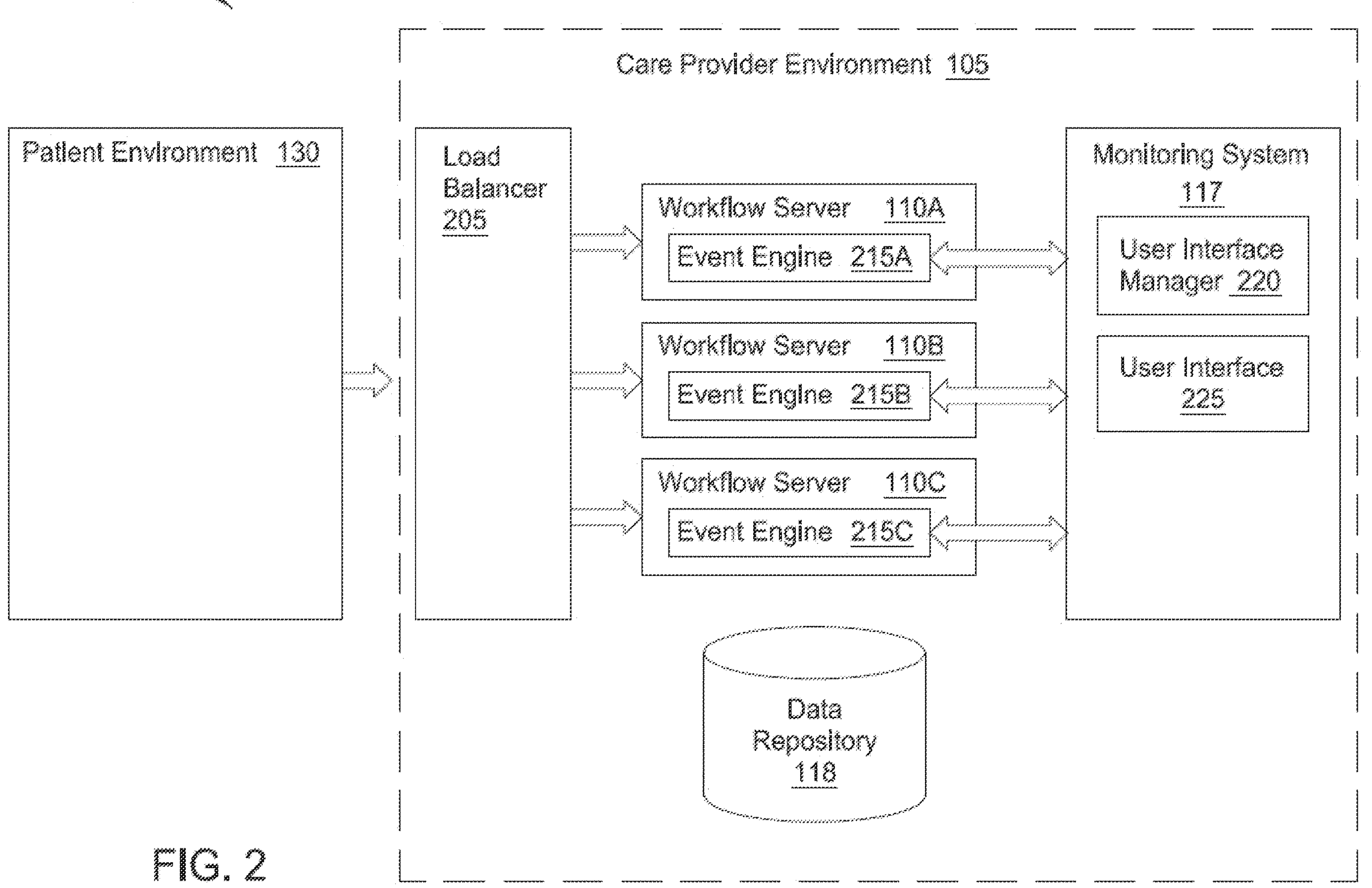
FIG. 2 illustrates a parallel processing computing environment, according to certain embodiments of the present disclosure.

FIG. 2 illustrates a parallel processing computing environment 200, according to one embodiment. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In embodiments, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
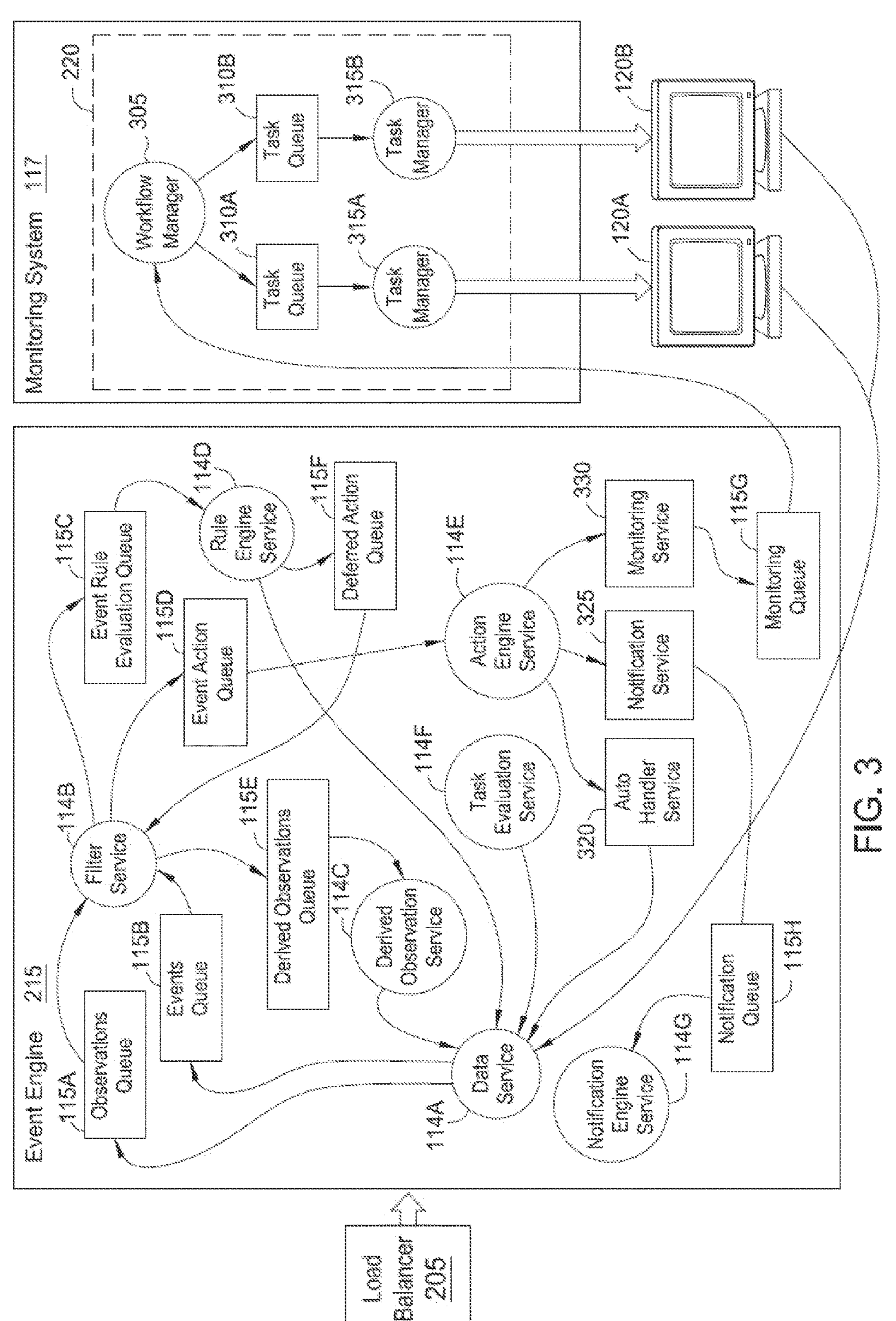
FIG. 3 illustrates an event engine for processing received health events, according to certain embodiments of the present disclosure.

FIG. 3 illustrates an event engine 215 that includes a workflow for processing health events, according to one embodiment. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 1158. This node 1148 serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 1148. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 1148 and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 320, notification service 325, or monitoring service 330. The auto handler service 320 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Figure 4:
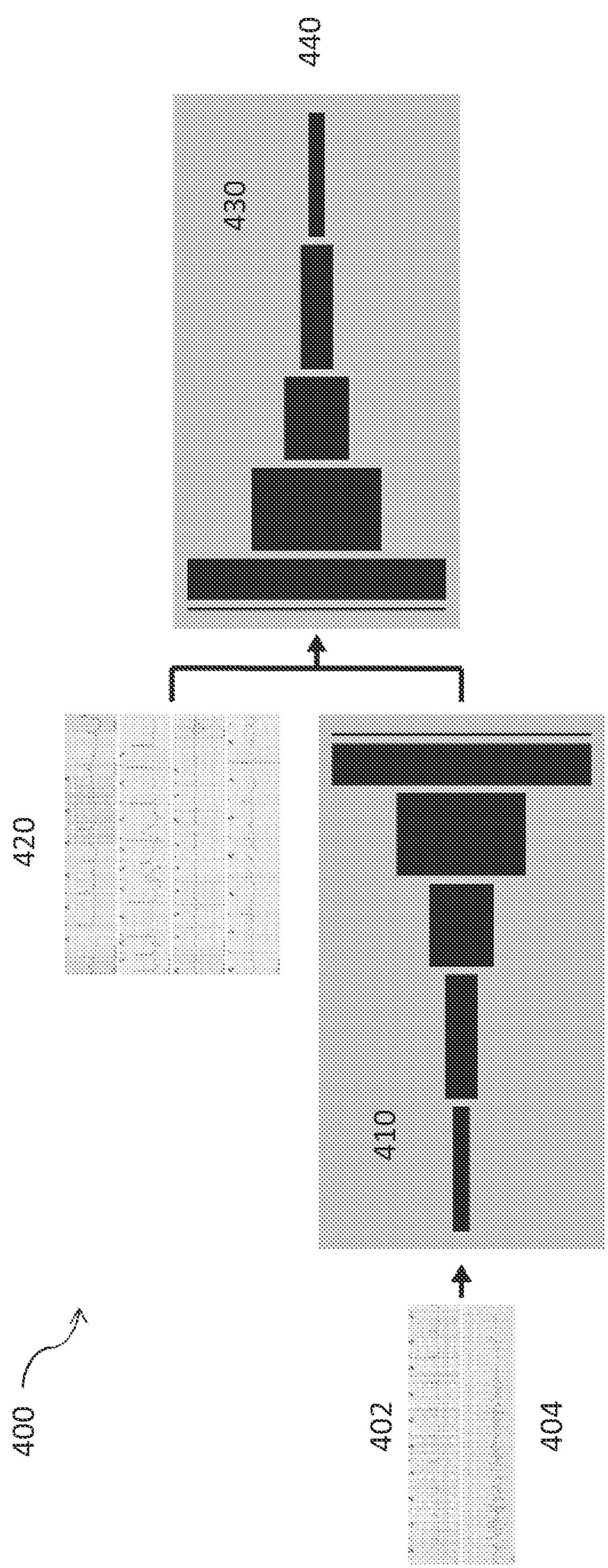
FIG. 4 illustrates a deep learning architecture for generating ECG training data with realistic noise, according to certain embodiments of the present disclosure.

FIG. 4 illustrates a deep learning architecture 400 for generating ECG training data with realistic noise, according to certain embodiments. In an embodiment, the deep learning architecture 400 includes two DNNs (e.g., convolutional DNNs, recurrent DNNs, or any other suitable DNNs). A generator DNN 410 generates ECG data with synthetic noise, while a discriminator DNN 430 discriminates between ECG data with real and synthetic noise. In an embodiment, the generator DNN 410 and the discriminator DNN 430 are co-trained so that the generator learns to create realistic synthetic noise and the discriminator learns to better differentiate between realistic and synthetic noise.

In an embodiment, clean ECG data 402 (e.g., data without noise) is provided to the generator DNN 410. Random noise 404 is also provided to the generator DNN 410. For example, the random noise 404 can be generated using a random number vector, causing the random noise 404 to vary based on the random number vector. In an embodiment, the random noise 404 is generated using any suitable technique, including with, or without, using an ML model.

In an embodiment, the generator DNN 410 uses the clean ECG data 402 and the random noise 404 to generate ECG data with realistic synthetic noise. For example, the generator DNN 410 can be a one-dimensional, or a two-dimensional, convolutional DNN, and can be trained to use single channel ECG data (e.g., single channel clean ECG data 402) or multi-channel ECG data (e.g., multi-channel clean ECG data 402). The generator DNN 410 can use, or exclude, any suitable combination of layers and connections, including down sampling convolution, de-convolution, pooling, batch normalization, dropout, a suitable non-linear activation function, residual connections, fully connected layers, or any other suitable layers or connections. Further, in an embodiment, the generator DNN 410 is provided with clean ECG data 402, which does not include any noise (e.g., naturally occurring noise has been removed).

The discriminator DNN 430 is then randomly provided either ECG data with synthetically added noise, output from the generator DNN 410, or real noisy ECG data 420 (e.g., real ECG data including naturally occurring noise). This is merely an example, and any suitable technique can be used to determine whether the discriminator DNN 430 is provided with output from the generator DNN 410 or rea noisy ECG data 420. In an embodiment, the discriminator DNN 430 attempts to determine whether the input is real noise ECG data (e.g., real noisy ECG data 420) or ECG data with synthetic noise (e.g., the output from the generator DNN 410). The discriminator DNN 430 generates an output 440 identifying whether the input ECG data includes real, or synthetic, noise.

In an embodiment the discriminator DNN 430 can be a one-dimensional, or a two-dimensional, convolutional DNN, and can be trained to use single channel ECG data (e.g., single channel noisy ECG data 420) or multi-channel ECG data (e.g., multi-channel noisy ECG data 420). The discriminator DNN 430 can use, or exclude, any suitable combination of layers and connections, including down sampling convolution, de-convolution, pooling, batch normalization, dropout, a suitable non-linear activation function, residual connections, fully connected layers, or any other suitable layers or connections. Further, in an embodiment, the discriminator DNN 430 is provided with noisy ECG data 420 (in random combination with the output from the generator DNN 410), which includes naturally occurring noise.

As discussed above, in an embodiment the generator DNN 410 and the discriminator DNN 430 are trained together, such that improvements in one DNN impact the other. This is a GAN architecture, in which adversarial DNNs are pitted against each other, and end up working in concert to improve the performance and accuracy of both DNNs. Improvements in the accuracy of the generator DNN 410 require the discriminator DNN 430 to make finer distinctions between real and synthetic noise added to ECG data, while improvements in accuracy of the discriminator DNN 430 cause the generator DNN 410 to be more realistic in generating synthetic noise, to better fool the discriminator DNN 430.

In an embodiment, simultaneous training of the generator DNN 410 and the discriminator DNN 430 does not require that both DNNs are operated at the same time. For example, the generator DNN 410 can be run to generate a sample of ECG data with synthetic noise and locked (e.g., paused), and then the discriminator DNN 430 can be run to determine whether its input was ECG data with real, or synthetic, noise. Further, in an embodiment, the generator DNN 410, the discriminator DNN 430, or both, can be partially trained separately. For example, the discriminator DNN 430 could be trained to identify uninterpretable data, or (as discussed below), to classify cardiac irregularities in the ECG data.

Further, in certain embodiments, the generator DNN 410 can receive feedback from the discriminator DNN 430, or vice-versa. For example, the generator DNN 410 can be provided both with the guess from the discriminator DNN 430 (e.g., real noise or synthetic noise) and a confidence level by the discriminator DNN 430 in the guess (e.g., a percentage or another suitable confidence value indicating the confidence of the discriminator DNN 430 in its guess). The generator DNN 410 can use the confidence level to further improve the realism of the generated synthetic noise. Similarly, the discriminator DNN 430 can receive a true value indicating whether the ECG data it received included real or synthetic noise, and thus what its output should have been and what the confidence level should have been. In an embodiment, the discriminator DNN 430 can include a loss function that minimizes, or reduces, the Euclidian distance between the confidence value in a guess and the true value.

In an embodiment, the generator DNN 410 and the discriminator DNN 430 are structured differently. For example, the discriminator DNN 430 can be structured to learn more slowly than the generator DNN 410, to facilitate improvement in the generator DNN 410. Further, in an embodiment, the generator DNN 410 is structured to start with a random number, or vector of random numbers, and generate a relatively large quantity of synthetic noise data. The discriminator DNN 430 is structured to go in the opposite direction, taking as input a relatively large quantity of ECG data with noise and generating a single output (e.g., real or synthetic). For example, the generator DNN 410 can employ convolution, while the discriminator DNN 430 can employ transposed convolution.

In an embodiment, the output 440 of the discriminator DNN 430 is an indication of whether the input includes real or synthetic noise. This is merely one example. Alternatively, or in addition, the output 440 can include additional information. For example, the discriminator DNN 430 could also be trained to identify cardiac irregularities in the ECG data (e.g., atrial fibrillation (AFib)) and to output both a value for the cardiac irregularity (e.g., present or not) and for the noise (e.g., real or synthetic).

Figure 5:
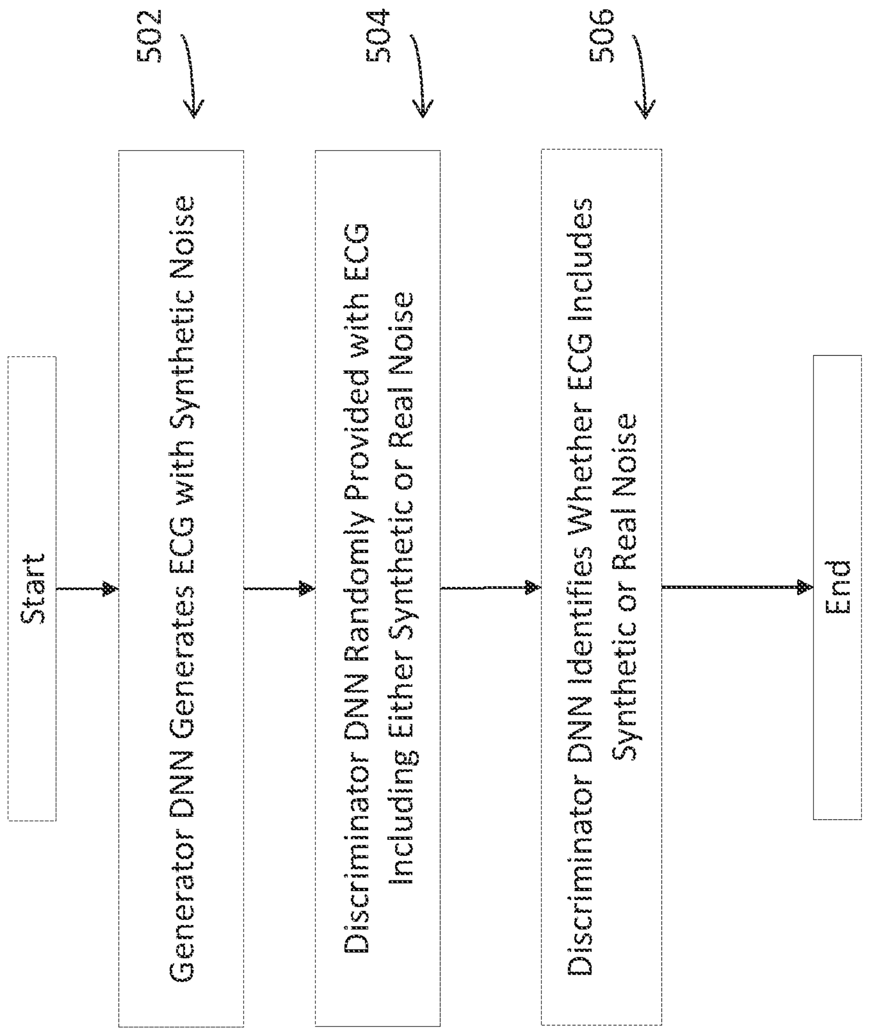
FIG. 5 is a flowchart illustrating using a deep learning architecture to generate ECG training data with realistic noise, according to certain embodiments of the present disclosure.
Figure 5:

FIG. 5 is a flowchart illustrating using a deep learning architecture to generate ECG training data with realistic noise, according to certain embodiments. At block 502, a generator DNN (e.g., the generator DNN 410 illustrated in FIG. 4) generates ECG data with synthetic noise. For example, the generator DNN can combine real, but clean, ECG data with randomly generated noise to generate ECG data with synthetic noise. This is discussed further below with regard to FIG. 6.

At block 504, a discriminator DNN (e.g., the discriminator DNN 430 illustrated in FIG. 4) is randomly provided with ECG data that includes either real noise, or synthetic noise. For example, as discussed above in relation to FIG. 4, the discriminator DNN can randomly be provided with either real noisy ECG data (e.g., real noise ECG data 420) or ECG data with synthetic noise (e.g., the output from the generator DNN 410).

At block 506, the discriminator DNN identifies whether the ECG includes synthetic or real noise. For example, as discussed above in relation to FIG. 4, the discriminator DNN can generate an output (e.g., the output 440) that indicates whether the input includes real or synthetic noise. Further, as discussed above, in an embodiment the discriminator DNN can identify a confidence level in this output (e.g., a confidence level in the accuracy of its guess). A generator DNN can use the output, and the confidence level (e.g., if available) to improve its generation of synthetic noise. And, as discussed above, the discriminator DNN can include a loss function to minimize the difference between its confidence level in its guess and the real truth.

Figure 6:
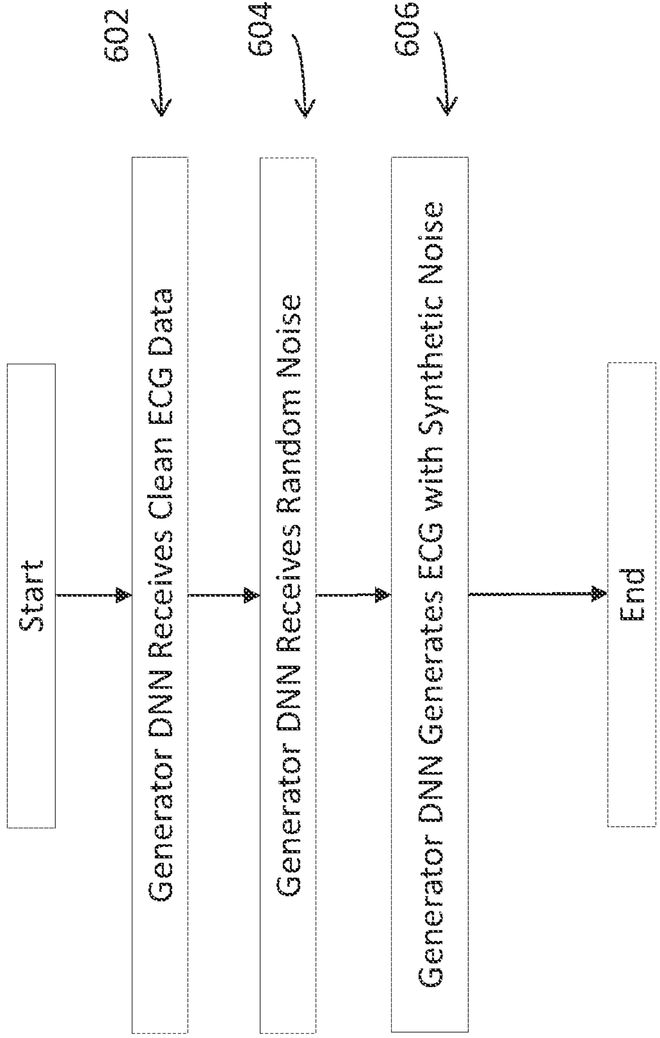
FIG. 6 is a flowchart further illustrating using a deep learning architecture to generate ECG training data with realistic noise, according to certain embodiments of the present disclosure.

FIG. 6 is a flowchart further illustrating using a deep learning architecture to generate ECG training data with realistic noise. In certain embodiments, FIG. 6 corresponds with block 502 in FIG. 5. At block 602, a generator DNN (e.g., the generator DNN 410 illustrated in FIG. 4) receives clean ECG data. For example, the generator DNN can receive clean ECG 402, illustrated in FIG. 4.

At block 604, the generator DNN receives random noise. For example, the generator DNN can receive random noise 404 illustrated in FIG. 4. As discussed above, in an embodiment the random noise is generated using a random number seed so that the noise varies across different operations of the generator DNN. Further, the random noise can be a random noise vector, a single random noise value, or any other suitable random noise.

At block 606 the generator DNN generates ECG data with synthetic noise. For example, the generator DNN adds to the clean ECG data synthetic noise generated using the random noise. In an embodiment, the generator DNN improves its generation of synthetic noise by co-training with a discriminator DNN, as discussed above in relation to FIG. 4.

Figure 7:
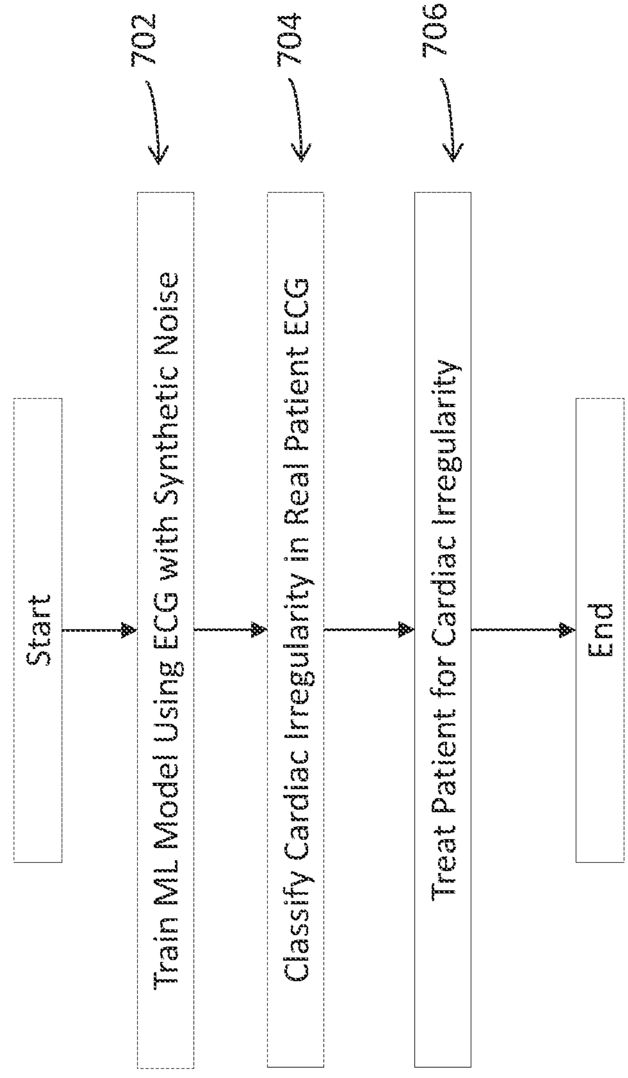
FIG. 7 is a flowchart illustrating training and using an ML model to identify a cardiac irregularity in a patient, according to certain embodiments of the present disclosure.

FIG. 7 is a flowchart 700 illustrating training and using an ML model to identify a cardiac irregularity in a patient. At block 702, an ML model (e.g., a DNN or any other suitable ML model) is trained using ECG data with synthetic noise. In an embodiment, a generator DNN (e.g., the generator DNN 410 illustrated in FIG. 4) is trained (e.g., co-trained with the discriminator DNN 430 illustrated in FIG. 4) to add realistic synthetic noise to a clean ECG. The generator DNN can be used to add a wide variety of synthetic noise to a given strip of clean ECG (e.g., without naturally occurring noise), or collection of strips of clean ECG. The ML model (e.g., a classifier ML model) can be trained using this ECG data with synthetic noise. In an embodiment, the use of synthetic noise significantly improves the training quality of the classifier ML model and improves accuracy and performance.

At block 704 the classifier ML model is used to classify cardiac irregularities in real patient ECG data. In an embodiment, the classifier ML model is trained (e.g., at block 702) using ECG data with synthetic noise. The trained classifier ML model can then be used to identify a cardiac irregularity in real patient ECG data.

At block 706, the patient can be treated for any cardiac irregularity. For example, devices in the computing environment (e.g., the computing environment 100 illustrated in FIG. 1) can then be used to treat the cardiac irregularity in the patient. For example, a particular medical treatment (e.g., a medication or a patient behavior) for the cardiac irregularity identified using the machine learning architecture could be recommended to the patient using the patient's mobile device (e.g., the mobile device 135 illustrated in FIG. 1). As another example, a report could be generated for a physician treating the patient, using the classified data. Alternatively, a report could be generated for the patient him or herself. Further, a patient care plan could be generated or modified based on the classified. For example, a patient care plan for a patient could be generated based on the classification. The patient care plan could provide medical treatment options (e.g., medication, educational content, behavioral changes, etc.) for the patient based on the classification. Further, an existing care plan for the patient could be modified.

In addition, an alert or output could be generated for the patient, care provider, or other interested parties. For example, an alert could be provided to the patient using a graphical user interface on a device operated by the patient (e.g., a mobile device 135 as illustrated in FIG. 1 or computer). Alternatively, an alert could be provided to the patient's care provider using a graphical user interface on a device operated by the care provider (e.g., a mobile device or a computing device 120 as illustrated in FIG. 1).

The ML models discussed above (e.g., both for generating ECG training data with synthetic noise and for identifying cardiac irregularities in a patient) can operate in a variety of locations. For example, an ML model can operate as part of the care provider environment 105 (e.g., on workflow server

110, computing device 120, or monitoring system 117). The model can operate on a dedicated computing system or a virtual computer instance (e.g., a cloud computing platform). Further, the ML model can operate on a device in the patient environment 130, including mobile device 135 and sensor devices 140. The ML model can be computationally intensive, however, and so the mobile device 135 or sensor devices 140 (or any of the devices in care provider environment 105) can include specialized hardware for training and running the deep learning model. To facilitate classification, the input and output of the ML model can be stored in a suitable location (e.g., the data repository 118 illustrated in FIG. 1).

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

I claim:

1. A computer-implemented method comprising:

inputting synthetic noise and naturally occurring electrocardiogram (ECG) data to a first deep neural network (DNN) to generate first ECG data;

providing one of: (i) the first ECG data, or (ii) second ECG data including naturally occurring noise, to a second DNN;

generating an output by the second DNN indicating whether the second DNN received the first ECG data or the second ECG data;

training the first DNN using the output;

generating, using the first DNN, training data to train a machine learning (ML) model to identify a cardiac irregularity in patient ECG data.

2. The computer-implemented method of claim 1, wherein the first DNN and the second DNN are co-trained, such that the first ECG data is used to train the second DNN and the output from the second DNN is used to train the first DNN.

3. The computer-implemented method of claim 1, wherein one of the first ECG data or the second ECG data is randomly provided to the second DNN.

4. The computer-implemented method of claim 1, wherein the first DNN uses ECG data without naturally occurring noise and randomly generated noise to generate the first ECG data.

5. The computer-implemented method of claim 1, wherein the output further comprises a confidence indicator.

6. The computer-implemented method of claim 1, further comprising:

generating third ECG data comprising synthetic noise using the trained first DNN; and training the ML model using the third ECG data.

7. The computer-implemented method of claim 6, further comprising:

identifying a cardiac irregularity in a patient using fourth ECG data and the trained ML model, wherein the fourth ECG data comprises naturally occurring ECG data from the patient and naturally occurring noise.

8. The computer-implemented method of claim 7, further comprising:

treating the patient based on the cardiac irregularity.

9. A non-transitory computer-readable medium containing computer program code that, when executed by a computer processor, performs an operation comprising:

inputting synthetic noise and naturally occurring electrocardiogram (ECG) data to generate first ECG data using a first deep neural network (DNN);

providing one of: (i) the first ECG data, or (ii) second ECG data including naturally occurring noise, to a second DNN;

generating an output by the second DNN indicating whether the second DNN received the first ECG data or the second ECG data;

training the first DNN using the output; and generating, using the first DNN, training data to train a machine learning (ML) model to identify a cardiac irregularity in patient ECG data.

10. The non-transitory computer-readable medium of claim 9, wherein the first DNN and the second DNN are co-trained, such that the first ECG data is used to train the second DNN and the output from the second DNN is used to train the first DNN.

11. The non-transitory computer-readable medium of claim 9, wherein one of the first ECG data or the second ECG data is randomly provided to the second DNN.

12. The non-transitory computer-readable medium of claim 9, wherein the first DNN uses ECG data without naturally occurring noise and randomly generated noise to generate the first ECG data.

13. The non-transitory computer-readable medium of claim 9, wherein the output further comprises a confidence indicator, and wherein the first DNN uses both the confidence indicator and the indication of whether the second DNN received the first ECG data or the second ECG data to generate the first ECG data.

14. The non-transitory computer-readable medium of claim 9, the operation further comprising:

generating third ECG data comprising synthetic noise using the trained first DNN;

training the ML model using the third ECG data; and identifying a cardiac irregularity in a patient using fourth ECG data and the trained ML model, wherein the fourth ECG data comprises naturally occurring ECG data from the patient and naturally occurring noise.

15. A system, comprising:

a computer processor; and a memory having instructions stored thereon which, when executed on the computer processor, performs an operation comprising:

inputting synthetic noise and naturally occurring electrocardiogram (ECG) data to generate first ECG data using a first deep neural network (DNN);

providing one of: (i) the first ECG data, or (ii) second ECG data including naturally occurring noise, to a second DNN;

generating an output by the second DNN indicating whether the second DNN received the first ECG data or the second ECG data;

wherein the output is used to further training the first DNN using the output; and generating, using the first DNN, training data to train a machine learning (ML) model to identify a cardiac irregularity in patient ECG data.

16. The system of claim 15, wherein the first DNN and the second DNN are co-trained, such that the first ECG data is used to train the second DNN and the output from the second DNN is used to train the first DNN.

17. The system of claim 15, wherein the first DNN uses ECG data without naturally occurring noise and randomly generated noise to generate the first ECG data.

18. The system of claim 15, wherein the output further comprises a confidence indicator, and wherein the first DNN uses both the confidence indicator and the indication of whether the second DNN received the first ECG data or the second ECG data to generate the first ECG data.

19. The system of claim 15, the operation further comprising:

generating third ECG data comprising synthetic noise using the trained first DNN;

training the ML model using the third ECG data; and identifying a cardiac irregularity in a patient using fourth ECG data and the trained ML model, wherein the fourth ECG data comprises naturally occurring ECG data from the patient and naturally occurring noise.

* * * * *